US008768436B2

(12) United States Patent
Nagao

(10) Patent No.: US 8,768,436 B2
(45) Date of Patent: Jul. 1, 2014

(54) CORONARY ARTERY ANGIOGRAPHY IMAGE PROCESSING METHOD TO DETECT OCCLUSION AND DEGREE EFFECT OF BLOOD VESSEL OCCLUSION TO AN ORGAN

(75) Inventor: Tomohiro Nagao, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 0 days.

(21) Appl. No.: 13/202,592

(22) PCT Filed: Feb. 26, 2010

(86) PCT No.: PCT/JP2010/053085
§ 371 (c)(1), (2), (4) Date: Aug. 22, 2011

(87) PCT Pub. No.: WO2010/098444
PCT Pub. Date: Sep. 2, 2010

(65) Prior Publication Data
US 2011/0306868 A1 Dec. 15, 2011

(30) Foreign Application Priority Data
Feb. 26, 2009 (JP) ................................ 2009-043320

(51) Int. Cl.
*A61B 5/05* (2006.01)

(52) U.S. Cl.
USPC ............................ 600/425; 600/485; 382/128

(58) Field of Classification Search
CPC .. A61B 5/02007; A61B 6/503; A61B 6/5217; A61B 6/504; G06T 2207/30104; G06T 2207/10081; G06T 2207/30048
USPC ........................................................ 600/410
See application file for complete search history.

(56) References Cited

U.S. PATENT DOCUMENTS

2006/0056685 A1 3/2006 Kiraly et al.
2007/0053555 A1* 3/2007 Ooi et al. ...................... 382/128
(Continued)

FOREIGN PATENT DOCUMENTS

| | | |
|---|---|---|
| JP | 2001-283191 | 10/2001 |
| JP | 2003-33349 | 2/2003 |
| JP | 2005-80942 | 3/2005 |
| JP | 2005-124614 | 5/2005 |
| JP | 2006-81906 | 3/2006 |

(Continued)

OTHER PUBLICATIONS

International Search Report in PCT/JP2010/053085.

*Primary Examiner* — Unsu Jung
*Assistant Examiner* — Serkan Akar
(74) *Attorney, Agent, or Firm* — Cooper & Dunham LLP

(57) ABSTRACT

By a CPU (101) of a device (100) for processing medical image, a coronary artery region and a cardiac muscle region that are to be analyzed are extracted from angiographic images of the coronary artery obtained from X-ray CT images or the like. Next, degrees of isolation (blood vessel dependences), which indicate the effects of the coronary artery on the individual sites of the myocardium, are calculated. The calculated degrees of isolation are referred to as pixel values and displayed while superimposed on a bull's eye map of the cardiac muscle, a three-dimensional image of the heart or the like. As a result, the effect of infarction or constriction on the cardiac muscle region can be visually recognized merely by using the angiographic image data of the coronary artery without conducting a delay angiographic imaging examination or the like.

8 Claims, 5 Drawing Sheets

(56) References Cited

U.S. PATENT DOCUMENTS

| | | | | |
|---|---|---|---|---|
| 2008/0118121 | A1* | 5/2008 | Skinner et al. ................ | 382/128 |
| 2008/0118122 | A1 | 5/2008 | Sirohey et al. | |
| 2009/0136107 | A1* | 5/2009 | Arnold et al. ................. | 382/131 |
| 2011/0295579 | A1* | 12/2011 | Tang et al. ........................ | 703/9 |

FOREIGN PATENT DOCUMENTS

| | | |
|---|---|---|
| JP | 2008-29735 | 2/2008 |
| JP | 2008-126078 | 6/2008 |
| JP | 2009-18005 | 1/2009 |
| JP | 2009-28362 | 2/2009 |

* cited by examiner

CORONARY ARTERY ANGIOGRAPHY IMAGE PROCESSING METHOD TO DETECT OCCLUSION AND DEGREE EFFECT OF BLOOD VESSEL OCCLUSION TO AN ORGAN

FIELD OF THE INVENTION

The present invention relates to a device and method for medical image processing capable of executing the process for analyzing a medical image.

DESCRIPTION OF RELATED ART

As for the conventional image to be used for medical diagnosis, a tomographic image, etc. of an object to be examined scanned by, for example an X-ray CT (Computed Tomography) apparatus or MRI (Magnetic Resonance Imaging) apparatus are commonly known. Also, a Computer-Aided Detection (hereinafter referred to as CAD) has been developed for analyzing such medical images using a computer so as to detect a lesion candidate from among the shadows therein to be presented to a doctor.

In recent years, as disclosed in Non-patent Document 1, the image processing method has been developed for generating images useful for diagnosis by scanning a heart region by a PET (Positron Emission Tomography) device, etc. for visualizing the lesioned part of a coronary artery using the nuclear medicine image thereof or by generating the image in which a nuclear medicine image and an X-ray CT image are combined using a computer.

Also, in order to visualize reflux flow of a cardiac muscle or cardiac muscle viability, examinations such as cardiac muscle perfusion or delayed contrast study have been conducted using, for example an MRI apparatus.

PRIOR ART DOCUMENT

Non-patent Document 1: RadFan Vol. 6, No. 13 (2008) P. 33, P. 81

However in an X-ray CT apparatus, it is not realistic to execute the delayed contrast imaging as mentioned above due to problems such as exposure to radiation. Also, while it is possible to acquire an image of an abnormal region caused by a coronary artery by the coronary artery angiography using an X-ray CT apparatus, acquisition of an image reflecting the effect of the coronary artery on the cardiac muscle has been difficult.

Also as mentioned above, the nuclear medicine image showing a lesioned part of a coronary artery scanned by a PET apparatus is generally superimposed on the image of a heart region scanned by an X-ray CT apparatus. Therefore the respective images need to be scanned separately which causes patients to bear a severe physical burden.

Further in an X-ray CT apparatus or MRI apparatus, in the case that a coronary artery is completely occluded, contrast agent cannot reach the coronary artery portion which is further distal than the occluded portion which makes it difficult to be depicted on an image. Therefore, it has been impossible to specify a cardiac muscle region affected by a constriction or embolism without executing a cardiac muscle perfusion or delayed contrast study.

The objective of the present invention is to provide the medical image processing device and method for generating an image that indicates the effect of blood vessels to an organ using an angiographic image of a coronary artery, etc. considering the above-described problems.

BRIEF SUMMARY OF THE INVENTION

In order to achieve the above-mentioned objective, the medical image processing device of the present invention comprises:

extraction means configured to extract a blood vessel region and an organ region from a medical image;

calculation means configured to calculate blood vessel dependence which indicates the degree of effect given by the blood vessel for each portion in the organ region extracted by the extraction means; and blood vessel dependence display means configured to generate and display the image indicating the blood vessel dependence calculated by the calculation means.

The medical image processing device is characterized in that the blood vessel dependence is calculated by the calculation means based on the distance data between each portion in the organ region and a portion in the blood vessel region and the data related to the blood flow volume in the blood vessel region.

Also, the calculation means of the medical image processing device, in the case that there is a constricted portion in the blood vessel region, calculates the blood vessel dependence with respect to the portion in the blood vessel region which is further distal than the constricted portion using the parameter showing the variance of the blood vessel volume caused by the constriction.

Also, the medical image processing device further comprises specification means configured to specify a blood vessel region or an arbitrary portion in the blood vessel region, wherein the blood vessel dependence display means generates and displays the image showing the blood vessel dependence calculated by the calculation means with respect to the blood vessel region specified by the specification means or the blood vessel region, in the case that a portion in the blood vessel region is specified, which is further distal than the specified portion.

Also, the medical image processing device of the present invention according to claim 1 further comprises:

simulation calculation means configured to assume an arbitrary portion in a blood vessel region as a constricted portion and calculate the blood vessel dependence, by varying the parameter indicating variance of the blood flow volume caused by the constriction stepwise, for each step with respect to the blood vessel region which is further distal than the assumed constricted portion; and simulation image display means configured to generate and display the predicted simulation image of a cardiac muscle infarction or angina pectoris using blood dependence of the respective steps calculated by the simulation calculation means.

Also, the medical image processing method of the present invention comprises:

an extraction step configured to extract a blood vessel region and an organ region from a medical image;

a calculation step configured to calculate blood vessel dependence which indicates the degree of effect given by the blood vessel for each portion in the organ region extracted by the extraction means; and a blood vessel dependence display step configured to generate and display the image indicating the blood vessel dependence calculated by the calculation step.

The medical image processing method is characterized in that the blood vessel dependence is calculated by the calculation step based on the distance data between each portion in the organ region and a portion in the blood vessel region and the data related to the blood flow volume in the blood vessel region.

Also, the calculation step of the medical image processing method, in the case that there is a constricted portion in the blood vessel region, calculates the blood vessel dependence with respect to the portion in the blood vessel region which is further distal than the constricted portion using the parameter showing the variance of the blood vessel volume caused by the constriction.

Also, the medical image processing method further comprises specification step configured to specify a blood vessel region or an arbitrary portion in the blood vessel region, wherein the blood vessel dependence display step generates and displays the image showing the blood vessel dependence calculated by the calculation means with respect to the blood vessel region specified by the specification step or the blood vessel region, in the case that a portion is specified in the blood vessel region, which is further distal than the specified portion.

Also, the medical image processing method of the present invention further comprises:

a simulation calculation step configured to assume an arbitrary portion in a blood vessel region as a constricted portion and calculate the blood vessel dependence, by varying the parameter indicating variance of the blood flow volume caused by the constriction stepwise, for each step with respect to the blood vessel region which is further distal than the assumed constricted portion; and a simulation image display step configured to generate and display the predicted simulation image of a cardiac muscle infarction or angina pectoris using blood vessel dependence of the respective steps calculated by the simulation calculation step.

EFFECT OF THE INVENTION

In accordance with the present invention, it is possible to provide the medical image processing device and method capable of generating the image showing the effect by a blood vessel to an organ using an angiographic image of a coronary artery and the like.

DETAILED DESCRIPTION OF THE INVENTION

An embodiment of the present invention will be described in detail based on the attached diagrams.

First, configuration of image processing system 1 to which the medical image processing device of the present invention is applied will be described referring to FIG. 1.

Figure 1:
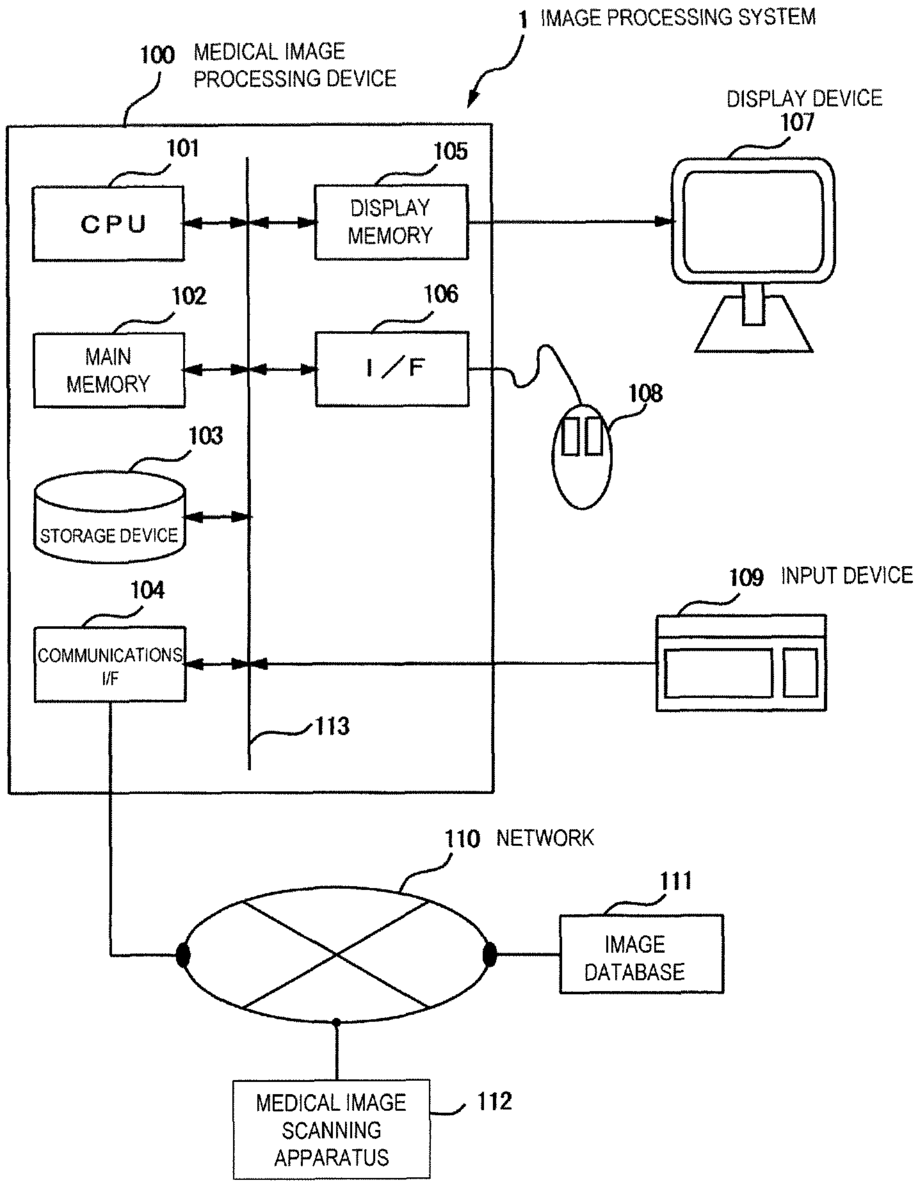
FIG. 1 is a hardware configuration diagram showing the general configuration of image processing system 1.

As shown in FIG. 1, image processing system 1 comprises medical image processing device 100 having display device 107 and input device 109, image database 111 connected to medical image processing device 100 via network 110 and medical image scanning apparatus 112.

Medical image processing device 100 is a computer for image diagnosis to be installed in a facility such as a hospital, for analyzing a medical image and generating an image appropriate for diagnosis.

Medical image processing device 100 comprises CPU (Central Processing Unit) 101, main memory 102, storage device 103, communications interface (Communications I/F) 104, display memory 105 and interface (I/F) 106 to be connected to an external device such as mouse 108, and the respective components are connected via bus 113.

CPU 101 calls up the program to be stored in main memory 102 or storage device 103 to a work memory region on a RAM of main memory 102 and executes the program, performs drive control on the connected respective components via bus 113, and works out various processing to be executed by medical image processing device 100.

Also, CPU 101 extracts a blood vessel region or organ region from a medical image, in an analysis process to be described later (refer to FIG. 2), calculates blood vessel dependence indicating degree of effect given by the blood vessel region with respect to each portion in the extracted organ region, generates and displays the image showing the calculated blood vessel dependence.

Main memory 102 is configured by ROM (Read Only Memory), RAM (Random Access Memory) and the like. ROM keeps program, data, etc. of a boot program or BIOS, etc. in a computer. on a permanent basis. Also, RAM temporarily keeps the program, data, etc. loaded from a device such as a ROM and storage device 103, and comprises the work area to be used for executing various processing.

Storage device 103 executes reading and writing of data for an HDD (Hard Disk Drive) or other storage device, and stores the program to be executed by CPU 101, the data necessary for executing the program, OS (Operating System), etc. The programs to be stored are a control program equivalent to the OS or an application program and the like. These respective program codes are read out as need arises and transmitted to the RAM in main memory 102 by CPU 101 to be executed as various means.

Communication I/F 104 has devices such as a communication controller and a transmission port, and transmits signal communication between medical image processing device 100 and network 110. Also, communications I/F 104 controls communication among image database 111 or other computers and medical image scanning apparatus 112 such as an X-ray CT apparatus or MRI apparatus via network 110.

I/F 106 is a port for connecting the peripheral devices, and executes transmission/reception of data to/from the peripheral devices. For example, a pointing device such as mouse 108 or a stylus pen may be connected to the medical image scanning apparatus via I/F 106.

Display memory 105 is a buffer for temporarily accumulating the display data inputted from CPU 101. The accumulated display data is outputted to display device 107 at a predetermined timing.

Display device 107 is configured by a display device such as a liquid crystal panel or CRT monitor and a logical circuit for executing display processing while being linked up with the display device, and is connected to CPU 101 via display memory 105. Display device 107 displays the display data accumulated in display memory 105 under control of CPU 101.

Input device 109 is an input device such as a keyboard, and outputs various commands or information inputted by an operator to CPU 101. The operator interactively operates medical image processing device 100 using external equipment such as display device 107, input device 109 and mouse 108.

Network 110 includes various communication networks such as a LAN (Local Area Network), WAN (Wide Area Network), Intranet and Internet, and transmits communication connection among image database 111, a server or other information equipment and medical image processing device 100.

Image database 111 accumulates and stores the medical image data scanned by medical image scanning apparatus 112, and is installed at a facility such as a hospital and a medical center. While image database 111 is connected to medical image processing device 100 via network 110 in medical image system 1 of FIG. 1, image database 111 may be provided in, for example storage device 103 in medical image processing device 100.

Next, operation of medical image processing device 100 will be described referring to FIG. 2~FIG. 5.

CPU 101 of medical image processing device 100 reads out programs and data related to analysis processing from main memory 102, and executes analysis processing based on the read out programs and data.

Upon starting of the analysis processing below, it is assumed that image data are loaded from image database 111, etc. via network 110 and communications I/F 104, and stored in storage device 103 of medical image processing device 100.

Figure 2:
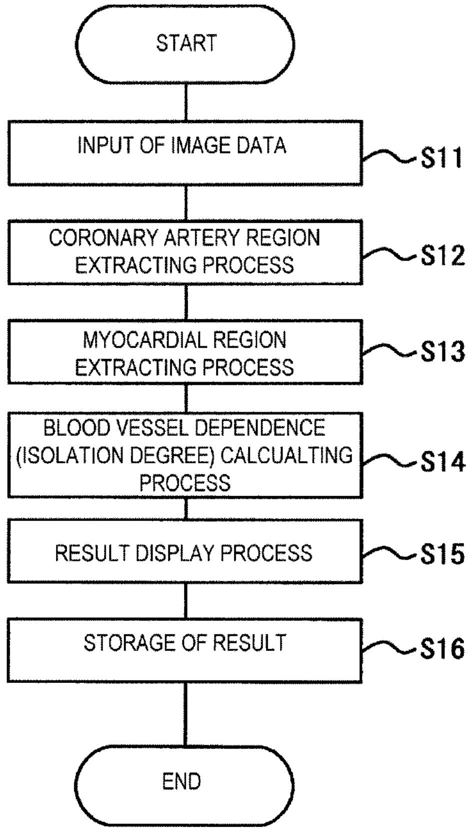
FIG. 2 is a flowchart showing the entire analysis processing to be executed by medical image processing device 100.

In analysis processing of FIG. 2, CPU 101 of medical image processing device 100 first reads out the medical image data as input image data (step S11). The medical image to be read in here is the image in which an organ or a blood vessel of the region to be a analysis target is scanned. In the present embodiment, a coronary angiographic image of a heart region will be used as a preferable example. The analysis target is not limited to a heart region, and any region such as a brain may be used. As for medical images, the images taken by an X-ray CT apparatus are preferable considering image accuracy or burden to be caused by examinations.

CPU 101 extracts a coronary artery region from the inputted image data (step S12). Description on the extraction will be omitted here since a commonly known method such as threshold value processing of CT values or the region growing process may be used.

Next, CPU 101 extracts a cardiac muscle region of a heart (step S13). As for the cardiac muscle region, a left ventricle wall is to be extracted in this example.

As for the cardiac muscle wall region, a pseudo-region may be determined from the axial image of the cardiac muscle region or a minor axis transverse image of the left ventricle using the method wherein an operator traces the contour manually via an input device such as mouse 108 or a stylus pen.

Next, CPU 101 calculates the blood vessel dependence (step S14).

Blood vessel dependence is the numerical value showing the degree of effect given to an organ by a blood vessel, and is referred also to as relative distance between an organ and a blood vessel. Here, the effect given to the extracted cardiac region (organ) by the extracted coronary artery (blood vessel) is calculated as the blood vessel dependence. The blood vessel dependence is calculated using the data of distance between the portion in the coronary artery and the respective portions in the cardiac muscle and the data in relation to the blood flow volume of the coronary artery.

In concrete terms, distance between the portion in the coronary artery and the respective portions in the cardiac muscle is obtained from real space coordinate data of a certain portion (Ci) in the extracted coronary artery and real space coordinate data of a certain portion (Mn) in the extracted cardiac muscle. Also as for the blood flow volume of the coronary artery, for example the cross-sectional area or vessel diameter of a certain portion (Ci) in the coronary artery is to be used.

In the case that the coronary artery is running near a certain portion (Mn) of the cardiac muscle, the blood vessel dependence of the portion (Mn) becomes greater. Also, when data Ai related to the blood flow volume of the coronary artery (e.g., blood flow volume in a certain portion Ci of a coronary artery, with “i” being a positional number, as explained below) is great, the blood vessel dependence in the portion (Mn) becomes greater.

In the present embodiment, in order to generate an image of the region having the blood flow volume smaller than the normal condition due to a constriction or infarction or the region in the cardiac muscle where contrast medium cannot reach due to constriction or infarction, the degree of isolation R(Mn) which indicates the reverse of the blood flow independence is acquired and the minimum value MinR(Mn) thereof is set as the pixel value.

Degree of isolation R(Mn) can be defined by expression (1) below.

[Expression 1]

$$R(Mn) = \frac{Dist(CiMn)}{Ai} \quad (1)$$

Here, Ai represents the blood flow volume in a certain portion Ci of a coronary artery (for example, the square value of the cross-sectional area or a vessel diameter in a certain portion Ci), and Dist(CiMn) represents the distance between a certain portion Ci of a coronary artery and a certain portion Mn of a cardiac muscle.

The “i” or “n” of the subscripts are positional numbers, which may be set, for example as 0~511, etc. if the pixel count of the image is 512.

CPU 101 calculates isolation degree R(Mn) with respect to all of the combinations in the respective regions Mn of the cardiac muscle and the respective regions Ci of the coronary artery, and determines the combination having the minimum value. The minimum isolation degree can be defined using expression (2) below.

[Expression 2]

$$MinR(Mn) = \underset{i}{\mathrm{Min}} \frac{Dist(CiMn)}{Ai} \quad (2)$$

CPU 101 defines the minimum isolation degree MinR(Mn) as the pixel value of the portion Mn.

CPU 101 calculates isolation degree MinR(Mn) using the above-described expression (2) with respect to the respective portions Mn of the cardiac muscle region extracted in step S13, and sets them as the pixel values.

As a result of calculation of the minimum isolation degree MinR(Mn), the cardiac muscle regions that are not close to the coronary artery have a greater pixel value in comparison with those of the other cardiac muscle regions.

As an example, the case will be described that there is an infarction due to a blood clot in a certain portion of a certain branch in a coronary artery and contrast agent cannot reach further from the infarction portion.

Figure 3:
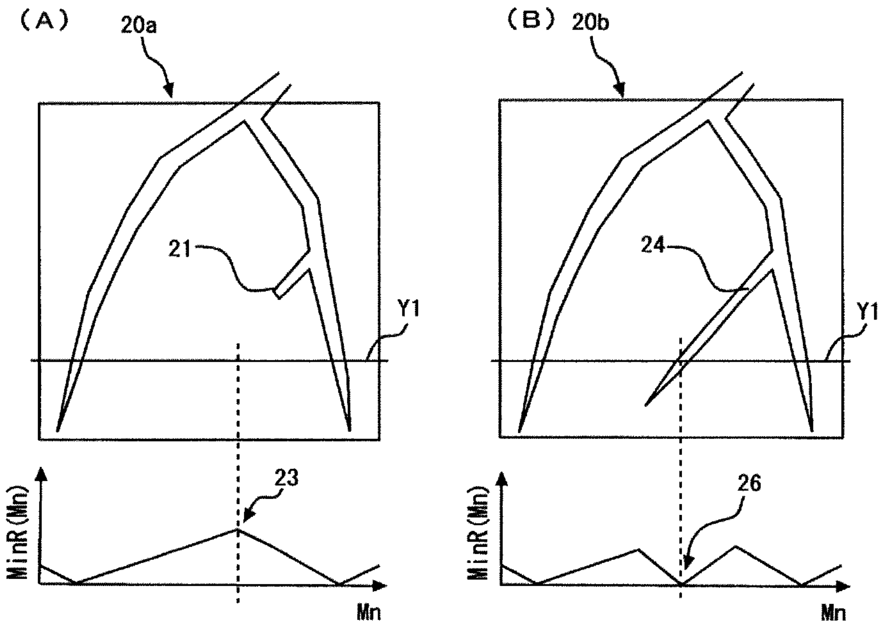
FIG. 3(A) is for explaining degree of isolation MinR(Mn) in the case that there is an infarction in a coronary artery.
FIG. 3(B) is for explaining degree of isolation MinR(Mn) in a normal state.

In this case, as shown in FIG. 3, it is difficult to extract the coronary artery which is further peripheral from the infarction portion from the input image data (coronary artery angiographic data), and the peripheral region of the coronary artery cannot be depicted on an image since there is no extraction data.

On the other hand, as described above, it is possible to depict the cardiac muscle region affected by the coronary artery which is further peripheral than an infarction portion by imaging the isolation degree MinR(Mn) acquired by expression (2) as the pixel value. In other words, the greater the isolation degree becomes, the greater pixel value can be acquired, whereby making it possible to generate the image using various display patterns by the method such as the threshold value processing of the pixel value and the volume rendering.

FIG. 3(A) shows the relationship between coronary artery image 20*a* in which an infarction portion on branch 21 of a coronary artery is depicted and isolation degree MinR(Mn), and FIG. 3(B) shows the relationship between a coronary artery image 20*b* in a normal condition and isolation degree MinR(Mn).

When comparing isolation degrees MinR(Mn) in the respective points Mn at the same Y positions (Y1) on images 20*a* and 20*b* between the case that there is an infarction as shown in FIG. 3(A) and the case of the normal blood vessel without an infarction as shown in FIG. 3(B), peak 23 of isolation degree MinR(Mn) appears between the two coronary arteries in the case that there is an infarction (FIG. 3(A)). This means that the possibility of the region having a small blood flow volume, i.e. the ischemic region is visualized.

On the other hand, in the case of a normal condition (FIG. 3(B)), blood vessel 24 is running through the same position (Y1), and isolation degree MinR(Mn) at the same Y position (Y1) as FIG. 3(A) results in a low value as shown in 26 of the graph.

While this sort of information could only be depicted on an image in the conventional techniques by executing scanning in the condition that the difference is obvious between the region in a cardiac muscle where contrast agent is accumulated and the region where contrast agent is not accumulated using, for example the delayed angiographic imaging by an MRI apparatus, by using the present method it is possible to depict the corresponding result without executing the delayed angiographic imaging and to estimate existence or nonexistence of the effect by an infarction to a cardiac muscle.

Figure 4:
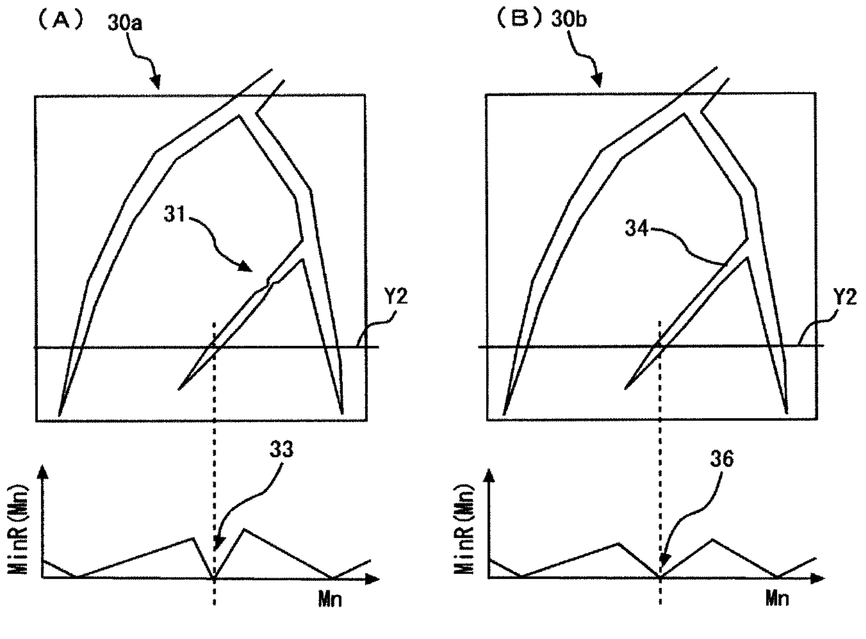
FIG. 4(A) is for explaining degree of isolation MinR(Mn) in the case that there is a constriction in a coronary artery.
FIG. 4(B) is for explaining degree of isolation MinR(Mn) in a normal state.

Also as another example, the case that there is a constriction in a certain portion of a coronary artery will be described referring to FIG. 4.

First, CPU 101 defines the degree of the constriction using the parameter indicating the variance of the blood flow volume caused by the constriction. In the present embodiment, for example ratio S($0<S<1$) is defined between the cross-sectional area in the normal condition and the actual cross-sectional area with respect to a certain portion Ci in a blood vessel. Here, the cross-sectional area in the normal condition is calculated from the extraction data of the coronary artery by performing interpolation, etc. on the cross-sectional area (or the diameter) in the vicinity of the target portion Ci. As for the ratio S, the ratio of the diameters of the constricted portions or the numeral values inputted by an operator may be used without using the actual cross-sectional areas.

As for the region in a coronary artery which is further distal than the constricted portion, since the constriction exerts the effect on the blood flow volume, amount Ai in relation to the blood flow volume is multiplied by the degree of constriction (ratio S) and applied to the above-described expression (1).

Then the isolation degree of the portion which is more peripheral than the constricted portion can be expressed by expression (3) below,

[Expression 3]

$$R(Mn) = \frac{Dist(CiMn)}{Ai \times S} \tag{3}$$

and the pixel value (the minimum isolation degree) can be expressed by expression (4) below.

[Expression 4]

$$MinR(Mn) = \min_i \left\{ \frac{Dist(CiMn)}{Ai \times S} \right\} \tag{4}$$

When there is a constriction in a coronary artery, CPU 101 obtains the isolation degree of the stem side portion in the blood vessel branch from the constricted portion using expression (2) and the isolation degree of the constricted portion and the portion which is the peripheral side of the branch from the constricted portion using expression (4).

Since the denominator in expression (4) includes ratio S($0<S<1$), the pixel value as the isolation degree tends to be greater in the peripheral side from the constriction. Such portions are estimated as receiving the effect of angina pectoris.

In image diagnosis, when the blood flow volume of a coronary artery increases in the condition that a heart is under strain, the increase of blood flow volume is blocked in the portion which is further distal than the constricted portion and supply of the blood including greater amount of oxygen compared to the cardiac region dependent on other normal coronary arteries is reduced, thus high possibility of lack of oxygen can be estimated.

When isolation degree MinR(Mn) in the respective points Mn at the same Y-position (Y2) on images 30*a* and 30*n* are compared between the case that there is constricted portion 31 as shown in FIG. 4(A) and the case of a normal condition without a constriction as shown in FIG. 4(B), in the case that there is a constriction of, for example 50% (S=0.5) in the cross-sectional area (FIG. 4(A)), portion 33 having a low isolation degree appears in the portion of the respective coronary arteries.

On the other hand, while portion 36 having a low isolation degree appears in the portion of the coronary arteries in the same manner also in the case of a normal condition (FIG. 4(B)), the variance of the degree is moderate compared with the case of FIG. 4(A). This means, when there is a constriction, that drastic change of the pixel value (isolation degree) can be recognized in the cardiac region which is affected by a constriction, and the range in the blood vessel which is affected by lack of oxygen can be estimated by observing such distribution of the pixel value.

When calculation of isolation degree MinR(Mn) in the entire cardiac region is completed in step S14, CPU 101 generates a display image by the method such as the volume rendering using the calculated isolation degree MinR(mn) as the pixel value, displays the generated image on display device 107(step S15), and stores the calculation result or the generated display image data in storage device 103 (step S16).

As for the method for visualizing cardiac viability, the method that displays cardiac viability as bull's eye map or a 3-dimensional image has been often used. In the result display processing in step S15, CPU 101 superimposes the image showing the isolation degree, for example over the bull's eye map, the 3-dimensional image of a cardiac muscle or the 2-dimensional image of the cross-section of the cardiac muscle in the minor-axis direction.

The bull's eye map is the display method which represents a heart on a concentric map and presents functional information, etc. of the heart on the polar coordinates of the depth and the angle. The distance from the center of the bull's eye map corresponds to the depth. The depth here means the cross-sectional position of the heart. Here, the bull's eye map is represented by setting the isolation degree of the respective cardiac portions calculated in step S14 as the pixel value.

The bull's eye map can be displayed using any display method such as the color map display, grayscale display, binarization display and transparency display. In the color map display, the color table in which the color value in accordance with the size (magnitude?) of the pixel value is prepared in advance and the color value in accordance with the isolation degree (pixel value) is allocated. The grayscale display represents the size of the pixel value by a grayscale. The binarization display binarizes the size of the pixel value using a predetermined threshold value, and displays on an image only the pixel values larger than the predetermined value or the pixel values smaller than the predetermined value. Also, the transparency display sums up the volume data (pixel value) of a 3-dimensional image in the eye direction using for example, the volume rendering method and displays the summed data while providing a predetermined transparency.

Also, a coronary artery may be superimposed and displayed over the bull's eye map or a 3-dimensional image in which the isolation degree is visualized in a predetermined display pattern. In this case, the portion of the coronary artery in the above-mentioned bull's eye map or 3-dimensional image is specified and superimposed from the coronary artery extraction data extracted in step S12.

Also, without visualizing the isolation degree of the entire cardiac muscle, the range of region affected by only the coronary artery which is specified by an operator (isolation degree) may be displayed. Also, an arbitrary portion of a coronary artery may be specified and the isolation degree may be displayed with respect to only the blood vessel region which is further distal than the specified portion.

Figure 5:
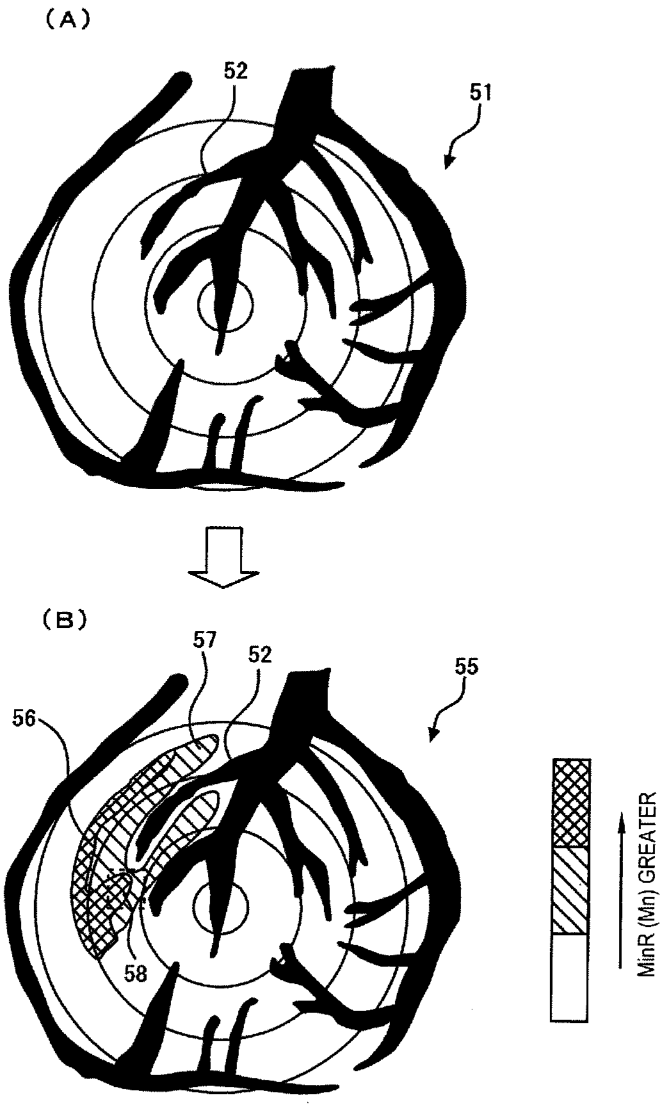
FIG. 5 is a display example using a bull's eye map.

FIG. 5 is a display example in the medical image processing device 100 related to the present invention.

In the result display processing of step S15 in FIG. 2, for example CPU 101 first displays image 51 as shown in FIG. 5(A). A coronary artery is superimposed over a bull's eye map in image 51 of this example. In this step, when a certain branch 52 of the coronary artery is specified through the operation of a pointing device such as mouse 108 by the operator, CPU 101 visualizes the isolation degree with respect to the specified branch 52.

FIG. 5(B) is image 55 in which the isolation degree with respect to the specified branch 52 is visualized. As shown in FIG. 5(B), regions 56 and 57 surrounding branch 52 are displayed by the respective predetermined display patterns. In this example, the isolation degree is represented in three stages as "no pattern", "oblique lines" and "shaded" in accordance with the value of isolation degree, and isolation degree MinR(Mn) becomes greater in the order thereof.

In FIG. 5(B), it is visualized that the isolation degree of region 57 denoted by oblique lines is smaller than that of regions 56 and 58. It can be visualized that the shaded regions 56 and 58 have large isolation degree. Particularly, it can be estimated that region 58 in region 56 surrounded by a frame border is an ischemic region due to a constriction or infarction since it is comparatively close to the portion in the coronary artery yet has a large isolation degree.

Also in the result display processing of step S15 in FIG. 2, CPU 101 may generate the estimated simulation image of a cardiac infarction or angina pectoris and display the generated image.

In the estimated simulation processing, CPU 101 estimates the constricted portion in a blood vessel, calculates the degree of isolation in each step of the progression of angina pectoris or cardiac infarction with respect to the blood vessel portion further distal than the estimated constricted portion, visualizes the isolation degree in the respective steps as described above, and displays the isolation degrees consecutively or by juxtaposing them.

Estimation of a constricted portion or an infarction portion in a blood vessel is executed by the command from an operator. Also, when the degree of isolation is to be calculated in each stage of the progression of angina pectoris or cardiac infarction, CPU 101 varies the degree of the constriction (ratio S) to be used for the above-described expression (4) stepwise such as 0.1, 0.3, 0.5, 0.7, 0.999.

As described above, CPU 101 of medical image processing device 100 extracts a blood vessel region (a coronary artery region) and an organ region (for example, a cardiac region) from the inputted medical image (for example, cardiac angiographic image data of a heart region), calculates the blood vessel dependence showing the degree of effect exerted by the blood vessel with respect to the respective portions in the organ region, and outputs them as an image. The blood vessel dependence is calculated based on the distance data between the respective portions in the organ region and the portion in the blood vessel region and the data in relation to the blood flow volume of the blood vessel region. Also, since the preferable pattern for imaging the blood vessel dependence is the isolation degree showing the relative distance between the blood vessel and the organ (distance considering the blood flow volume), CPU 101 calculates the isolation degree by dividing the distance data between the respective portions in the organ region and the portion in the blood vessel region by the data in relation to the blood vessel volume of the blood vessel region (cross-sectional area or diameter of the blood vessel).

As a result, the degree of effect by a blood vessel to an organ can be easily visualized from a blood vessel angiographic image without conducting a delayed angiographic examination whereby making it possible to drastically reduce the burden of a patient.

Also in the case that a certain portion in a coronary artery is completely occluded, the effect by the blood vessel to the organ can be visualized with respect to the blood vessel region which is further distal than a infarction portion which cannot be depicted on a blood vessel angiographic image, which contributes the diagnosis.

While the case of applying the analysis processing with respect to an image of a heart region is exemplified above, the region is not limited thereto, and the blood vessel dependence may be visualized using images of other organs such as a brain.

Also, the display pattern of the images in which the blood vessel dependence is generated is not limited to the exemplified bull's eye map or a 2-dimensional or 3-dimensional image, and the image generation based on the blood vessel dependence disclosed in the present invention can be applied also to the commonly known display methods or the display methods to be developed in the future.

The preferable embodiments of the medical image processing device according to the present invention have been described above. However, the present invention is not limited to these embodiments. It is obvious that persons skilled in the art can make various kinds of alterations or modifications within the scope of the technical idea disclosed in this application, and it is understandable that they belong to the technical scope of the present invention.

DESCRIPTION ON THE REFERENCE NUMERALS

1: image processing system, 100: medical image processing device, 101: CPU, 102: main memory, 103: storage device, 104: communications I/F, 105: display memory, 106: I/F, 107: display device, 108: mouse (external equipment), 109: input device, 110: network, 111: image database, 112: medical image scanning apparatus, 20*a*, 20*b*, 30*a* and 30*b*: coronary artery angiographic image, 51: bull's eye map on which an artery coronary image is superimposed, 55: bull's eye map on which the blood vessel dependence (degree of isolation) is displayed.

The invention claimed is:

1. A medical image processing device comprising a processing unit and a non-transitory computer readable medium storing one or more programs of instructions executable by the processing unit to configure the processing unit to perform a method including:

(a) calculating blood vessel dependence indicating degree of an effect exerted by a blood vessel region extracted from a medical image with respect to each port on n an organ region extracted from the medical image, wherein the blood vessel dependence is calculated based on distance data between a portion of the blood vessel on the one hand and on the other hand respective portions in the organ region; and (b) generating and causing the image to be displayed showing the blood vessel dependence calculated in (a), wherein the blood vessel dependence is calculated in (a) based on the formula $$\operatorname*{Min}_{i} \frac{\mathrm{Dist}(CiMn)}{Ai},$$

wherein the blood vessel region includes Z portions, the organ region includes N portions, Mn is n-th portion of the organ region where each of Z, N and n is a positive integer, Ci is i-th portion of the blood vessel and "Min" is minimum operator applied to Z values of $$\frac{\mathrm{Dist}(CiMn)}{Ai},$$

with i being each positive integer from 1 to Z, "Dist(CiMn)" is the distance data between the n-th portion Mn in the organ region and the i-th portion Ci of the blood vessel region, Ai is blood flow volume in the i-th portion Ci of the blood vessel region.

2. The medical age processing device according to claim 1, wherein in cases where there is a constricted portion in the blood vessel region, the blood vessel dependence is calculated in (a) with respect to the blood vessel region further distal than the constricted portion using a parameter indicating variation of the blood flow volume caused by the constriction.

3. The medical image processing device according to claim 1, wherein the processing unit is further configure by the programs executed by the processing unit to (c) specify a blood vessel region or an arbitrary region in a blood vessel region, and (d) generate and display the image showing the blood vessel dependence calculated in (a) with respect to the blood vessel region specified in (c) or, in cases where a portion in a blood vessel region is specified, the blood vessel region which is further distal than the specified portion in the blood vessel region.

4. The medical image processing device according to claim 1, wherein the processing unit is further configure by the programs executed by the processing unit to include:

(e) calculate, based on assumption of an arbitrary portion in a blood vessel as a constricted portion, the blood vessel dependence, by varying the parameter indicating variation of blood flow volume caused by constriction stepwise, for each step with respect to the blood vessel which is further distal than the assumed constricted portion; and (f) generate and display an estimated simulation image of cardiac infarction or angina pectoris using the blood vessel dependence of the respective steps calculated in (e).

5. A medical image processing method performed by a medical image processing device, the method comprising:

extraction step performed by the medical image processing device to extract a blood vessel region and an organ region from a medical image;

calculation step performed by the medical image processing device to calculate the blood vessel dependence indicating degree of an effect exerted by the blood vessel region with respect to each portion in the organ region extracted by the extraction step, wherein the blood vessel dependence is calculated based on distance data between a portion of the blood vessel on the one hand and on the other hand respective portions in the organ region; and blood vessel dependence display step performed by the medical image processing device to generate and display the image showing the blood vessel dependence calculated by the calculation step, wherein the blood vessel dependence is calculated in the calculation step based on the formula $$\operatorname*{Min}_{i} \frac{\mathrm{Dist}(CiMn)}{Ai},$$

wherein the blood vessel region includes Z portions, the organ region includes N portions, Mn is n-th portion of the organ region, where each of Z, N and n is a positive integer, Ci is i-th portion of the blood vessel and "Min" is minimum operator applied to Z values of $$\frac{\text{Dist}(CiMn)}{Ai},$$

with i being each positive integer from 1 to Z, "Dist(CiMn)" is the distance data between the n-th portion Mn in the organ region and the i-th portion Ci of the blood vessel region, Ai is blood flow volume in the i-th portion Ci of the blood vessel region.

6. The medical image processing method according to claim 5, wherein the calculation step, in cases where there is a constricted portion in the blood vessel region, calculates the blood vessel dependence with respect to the blood vessel region further distal than the constricted portion using a parameter indicating variation of the blood flow volume caused by the constriction.

7. The medical image processing method according to claim 5, further comprising specification step performed by the medical image processing device to specify a blood vessel region or an arbitrary portion in the blood vessel region, wherein the blood vessel dependence display means generates and displays the image showing the blood vessel dependence calculated by the calculation step with respect to the blood vessel region specified by the specification step or, in cases where a portion is specified in a blood vessel, the blood vessel region further distal than the specified portion in the blood vessel region.

8. The medical image processing method according to claim 5, further comprising:

simulation calculation step performed by the medical image processing device to assume an arbitrary portion in a blood vessel as a constricted portion, and calculates the blood vessel dependence, by varying a parameter indicating variation of blood flow volume caused by the constriction stepwise, for each step with respect to the blood vessel region which is further distal than the assumed constricted portion; and simulation image display step performed by the medical image processing device to generate and display an estimated simulation image of cardiac infarction or angina pectoris using the blood vessel dependence of the respective steps calculated by the simulation calculation step.

* * * * *